(12) United States Patent
Lin et al.

(10) Patent No.: US 8,829,150 B2
(45) Date of Patent: Sep. 9, 2014

(54) METHODS FOR POLYMERING HAPTENS INTO IMMUNOGENS

(71) Applicant: National Taiwan Normal University, Taipei (TW)

(72) Inventors: Che-Hsiung Lin, Taipei (TW); Yu-Chie Wang, Taipei (TW)

(73) Assignee: National Taiwan Normal University, Taipei (TW)

( * ) Notice: Subject to any disclaimer, the term of this patent is extended or adjusted under 35 U.S.C. 154(b) by 0 days.

(21) Appl. No.: 14/031,062

(22) Filed: Sep. 19, 2013

(65) Prior Publication Data

US 2014/0088286 A1    Mar. 27, 2014

(30) Foreign Application Priority Data

Sep. 21, 2012   (TW) ............... 101134666 A

(51) Int. Cl.
| | | |
|---|---|---|
| *C08G 12/30* | (2006.01) | |
| *C08G 12/32* | (2006.01) | |
| *A61K 39/385* | (2006.01) | |
| *C08G 75/00* | (2006.01) | |
| *A61K 39/00* | (2006.01) | |

(52) U.S. Cl.
CPC ............ *C08G 12/32* (2013.01); *A61K 2039/64* (2013.01); *A61K 2039/6093* (2013.01); *A61K 39/385* (2013.01)
USPC .......................... 528/254; 530/300; 530/391.1

(58) Field of Classification Search
USPC ................................ 528/254; 530/300, 391.1
See application file for complete search history.

(56) References Cited

U.S. PATENT DOCUMENTS

2011/0217320 A1*   9/2011   Ennifar et al. ............. 424/175.1
2012/0295287 A1*   11/2012   Kellermann et al. ........ 435/7.93

FOREIGN PATENT DOCUMENTS

CN         101407580 B     6/2011

OTHER PUBLICATIONS

Zhu et al., "The analysis of immunological properties of glutaraldehyde-polymerized porcine hemoglobin", Journal of Northwest University (Natural Science Edition), Feb. 2011, vol. 41, No. 1, pp. 82-84.
Franciso Bonas-Cuesta et al.,"Enhancement of peptide immunogenicity by linear polymerization", Eur. J. Immunol. 1988. 18: 199-202.
Song et al., "Hapten Design Modification and Preparation of Artifical Antigens", Chinese Journal of Analytical Chemistry, Aug. 2010, vol. 8, No. 38, Sichuan University, pp. 1211-1218.

* cited by examiner

*Primary Examiner* — Terressa Boykin
(74) *Attorney, Agent, or Firm* — Bacon & Thomas, PLLC

(57) ABSTRACT

The present invention discloses methods for polymerizing non-immunogenic haptens into immunogens, which then can be used to stimulate anti-hapten antibody production in animals. Specifically, haptens with amine and/or carboxylic groups are polymerized into macromolecules by using crosslinking reagents, and the derived haptenic polymers are used to immunize animals for the production of anti-hapten antibodies.

12 Claims, 3 Drawing Sheets

METHODS FOR POLYMERING HAPTENS INTO IMMUNOGENS

CROSS REFERENCE TO RELATED APPLICATION

This application claims the benefits of the Taiwan Patent Application Serial Number 101134666, filed on Sep. 21, 2012, the subject matter of which is incorporated herein by reference.

BACKGROUND OF THE INVENTION

1. Field of the Invention

The present invention relates to methods for polymerizing haptens into immunogens, more particularly, to methods for polymerization of haptens into polymers having molecular weight greater than 4,000 Da, which can be used as immunogens for anti-hapten antibodies production.

2. Description of Related Art

An immunoassay is a biochemical test often used in medical diagnoses, food inspections and environmental examinations for its benefits of high sensitivity, specificity, time-efficiency, cost-effectiveness, and easy operation. In generally, test samples as antigens are injected into animals to stimulate the immune system to generate corresponding antibodies. However, some of the test samples are too small in sizes and incapable by themselves to provoke antibody production in animals. In these cases, the test samples are considered lacking of immunogenicity, and usually known as haptens. To elicit antibody production against hapten in animals, one commonly used protocol is to conjugate hapten onto a carrier protein and with which the animals are immunized. However, this approach has its limitations, such as the needs of an appropriate carrier and a suitable chemical cross-linker, which are not always easily available. Also, to gain reproducible coupling results, well-trained laboratory personnel are required for the coupling reactions often involve intricate chemical modifications of the coupled molecules. Moreover, even the coupling chemistry is successful and the immune system of the injected animal is responsive to the hapten-carrier complex, the proportion of anti-hapten antibodies to anti-carrier antibodies in the serum may still be too small to be effective because of low hapten density of the synthesized conjugate. As a result, the purification of anti-hapten antibodies becomes difficult and costly. Therefore, it is desirable to develop an easier and more efficient alternative for the production of anti-hapten antibodies.

In the present invention, we provide methods for directly polymerizing small and non-immunogenic haptens into immunogenic antigens. This invention not only simplifies the procedures of haptenic antigen preparation but also eliminate the involvement of carriers and their concomitant problems.

SUMMARY OF THE INVENTION

The present invention provides methods of polymerizing haptens into immunogens, including the steps of: (A) providing a hapten-containing solution, wherein haptens in the hapten-containing solution are chemical compounds with two or more amine groups, chemical compounds with two or more carboxylic groups, or chemical compounds with one or more amine group and one or more carboxylic group; (B) adding a cross-linking reagent into the hapten-containing solution to polymerize the haptens to obtain an immunogen with molecular weight greater than 4,000 Da.

In the step (B) of the method of the present invention, when the haptens are the chemical compounds having two or more amine groups, the cross-linking reagent is at least one selected from the group consisting of dialdehyde, polyaldehyde, bis-carboxylic acid, and poly-carboxylic acid; when the haptens are the chemical compounds having two or more carboxylic groups, the cross-linking reagent is at least one selected from the group comprising glycol, polyol, bis-amine, and polyamine; and when the haptens are the chemical compounds having one or more amine group and one or more carboxylic group, the haptens are polymerized with the cross-linking reagent of 1-ethyl-3-(3-dimethyl aminopropyl)-carbodiimide (EDC) or the amine group and the carboxylic group are cross-linked to each other through a dehydration reaction.

Further, in the step (A) of the method of the present invention, the hapten concentration used can be $1\times10^{-10}$ mM to the maximum soluble concentration of the happen, but preferably be $1\times10^{-10}$ mM to 300 mM. In the step (B), the concentration of cross-linking reagent concentration used can be $1\times10^{-10}$ mM or more, but preferably be 125 mM to 300 mM.

The reaction temperature is one important factor for the polymerization reactions. In the step (B) of the method of the present invention, the polymerization is performed at a temperature that the haptens can keep stable. Preferably, the haptens are polymerized at a temperature ranging from 4° C. to 80° C. More preferably, the haptens are polymerized at a temperature ranging from 37° C. to 80° C.

In one preferred embodiment of the present invention, the non-immunogenic melamine is polymerized into an immunogen directly, and the immunogen is injected into animals to stimulate the immune systems thereof to produce the subject antibodies. Melamine has three amine groups, and glutaraldehyde is used as the cross-linking reagent to polymerize the melamine into a macromolecular polymer. The polymerization of the melamine is shown in the following scheme I.

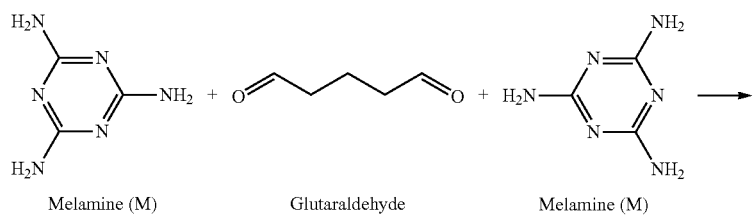

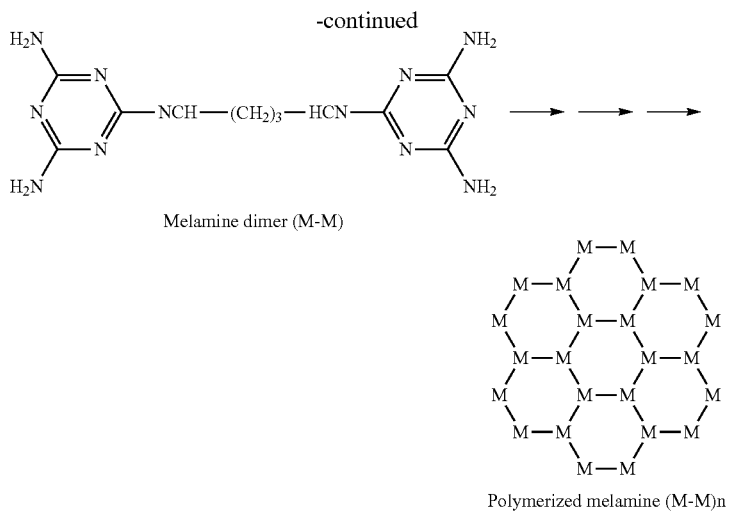

Melamine dimer (M-M)

Polymerized melamine (M-M)n

Herein, a melamine concentration in the melamine-containing solution is $1\times10^{-10}$ mM to 24 mM, for which it is preferred to be $1\times10^{-7}$ mM to 20 mM; and a glutaraldehyde concentration in the melamine-containing solution is $1\times10^{-10}$ mM to 300 mM, for which it is preferred to be $1\times10^{-7}$ mM to 300 mM, and it is more preferred to be 125 mM to 250 mM. In addition, the temperature for polymerization the melamine is above 0° C., and it is preferred to be 4° C. to 80° C.

A more detailed reaction condition is described as follows. At the beginning of the reaction, 0.9 mL of a melamine solution (20 mM) is mixed with 0.1 mL of glutaraldehyde (2.5 M). After 3-day incubation at 37° C., a white precipitate can be observed. The technique of Gel Permeation Chromatography (GPC) is then used to measure the molecular size of the precipitate, wherein the observed average molecular weight thereof is 17,842 Da, the average molecular weight thereof having the lowest 10% average molecular weight is 4,067 Da, and the average molecular weight thereof having the highest 10% average molecular weight is 75,483 Da. These results indicate that haptenic melamine can be polymerized, through the aforementioned polymerization reaction, into macromolecules that can meet the general size criteria of an immunogen.

After repeatedly immunizing animals (rabbits and mice) with the polymerized melamines produced by the method of the present invention, animal sera are collected and analyzed for the presence of anti-melamine antibodies. The results of immunoassays confirm the effectiveness of the polymerized melamine in stimulating animals' immune systems. Furthermore, the results of another immunoassay, by using the same antisera, reveal the detection limit of melamine can be as low as 1.8 ppb.

Based upon the concepts and methods disclosed by the present invention, a haptenic molecule, such as peptide, protein, hormone, enzyme, drug, and toxicant comprising amine groups and/or carboxylic groups might be polymerized into macromolecule with a cross-linking reagent, and then used as an immunogen for the production of anti-hapten antibodies.

DETAILED DESCRIPTION OF THE PREFERRED EMBODIMENT

Embodiment 1

Polymerization Reaction

Figure 2:
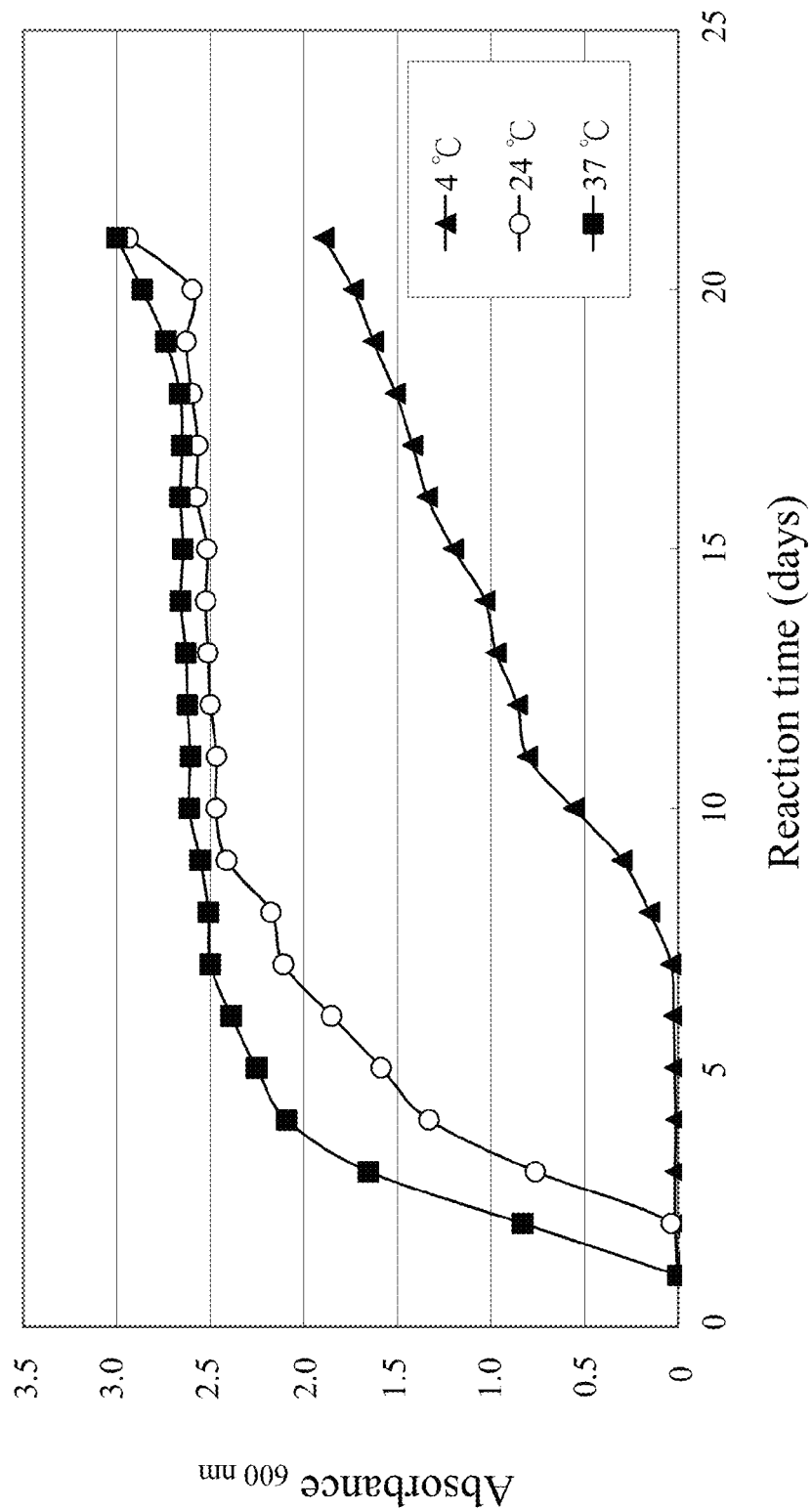
FIG. 2 is a diagram showing the relationship between temperature and the polymerization reaction of melamine in Embodiments 1~3.

Prepared 0.9 mL of 20 mM melamine (2.52 mg in 1 mL $H_2O$) in a glass vial and added to it 0.1 mL of 2.5 M glutaraldehyde, followed by incubation at 37° C. White precipitates, which are polymerization product of melamine, was observable after 3 days, and the polymerization degree of melamine reached to its plateau after 7 days (FIG. 2).

<Analysis of the Proportion of Polymerized Melamine>

Figure 1:
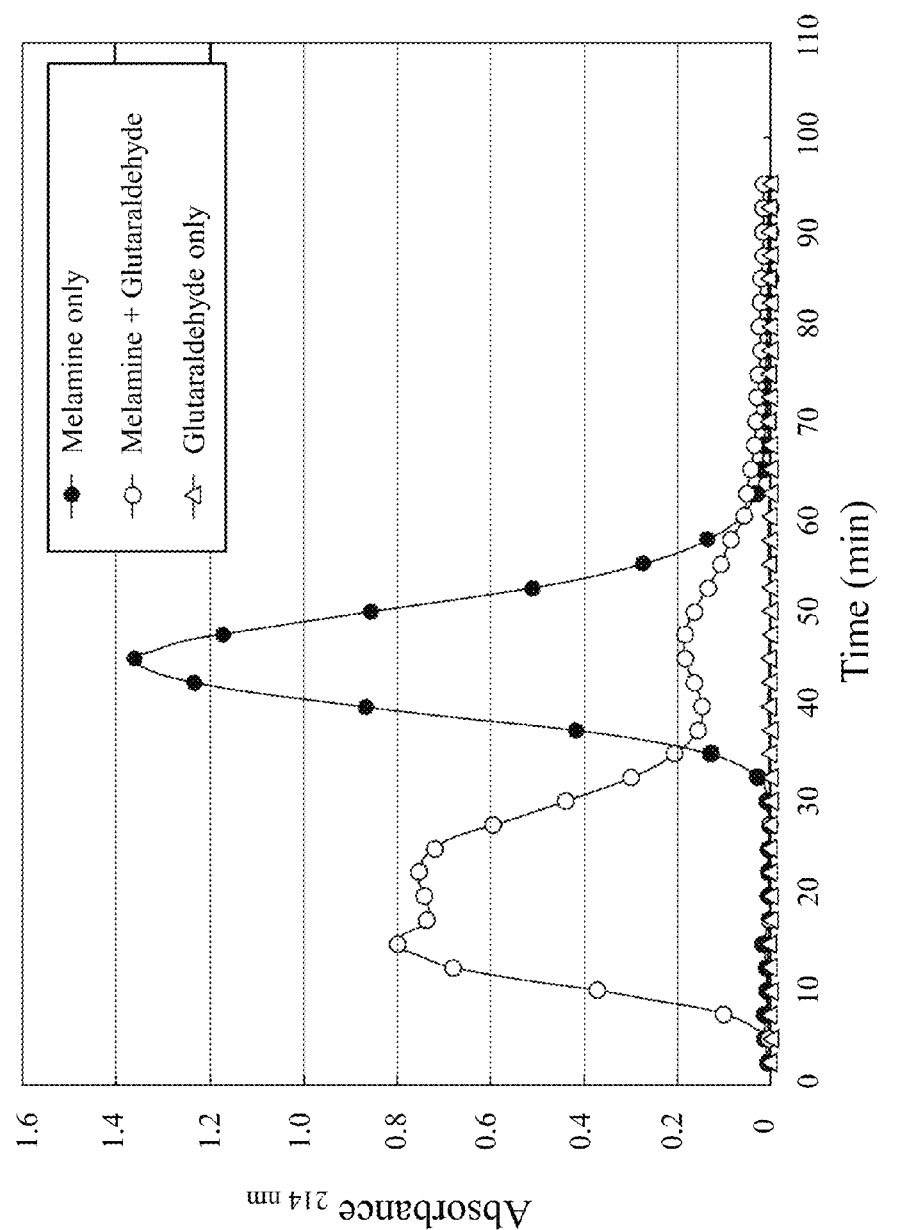
FIG. 1 is a diagram showing the analysis results of the proportion of the polymerized melamine in Embodiment 1.

After polymerizing for 3 days at 37° C., 20 µL of the reaction sample was loaded onto a G-10 column and eluted with water at a flow rate of 0.4 mL/min. Fractions of 1 mL were collected and to each of them the UV absorbance at 214 nm was measured. Other than the reaction sample, 20 µL of 18 mM melamine and 20 µL of 250 mM glutaraldehyde, as controls, were also added to and eluted from the G-10 column respectively, using the same conditions as described above. The elution profiles of all three aforementioned samples are shown in FIG. 1, and from which it is estimated that ca. 28% of melamine in the polymerization reaction sample remains as free form molecules, while the rest is in polymerized forms.

<Analysis of the Size of Polymerized Melamine>

After polymerization (37° C., 3 days), the polymerized melamine was separated with a centrifuge (10,000 g, 10 min) and the obtained precipitated was rinsed with water twice. Then, the precipitate was re-dissolved in 0.5 mL of dimethyl fumarate (DMF). The re-dissolved polymerized melamine solution was then injected into Gel Permeation Chromatography (GPC), and the analysis conditions were as follows: the chromatography column was Jordi gel DMF (polydivinylbenzene), 0.3% of lithium bromide solution in DMF was used as a mobile phase, and the flow rate of the lithium bromide solution was 1 mL/min. The analysis results indicate that the average molecular weight of the polymerized melamine is 17,842 Da, wherein the average molecular weight thereof having the lowest 10% average molecular weight is 4,067 Da, and the average molecular weight thereof having the highest 10% average molecular weight is 75,483 Da. Therefore, the molecular weight of the polymerized melamine is higher than 4,000 Da, which meets the size criteria for being an immunogen, so that the polymerized melamine obtained in the present embodiment has the potential to be used directly to stimulate anti-melamine antibodies production in animals.

Embodiments 2~9

In the present embodiments 2~9, melamine were polymerized under different conditions shown in table 1; wherein the term "reaction time" means the time that the precipitate can be observed.

TABLE 1

|  | Melamine | Glutaraldehyde | Reaction temperature | Reaction time |
|---|---|---|---|---|
| Embodiment 2 | 18 mM | 250 mM | 24° C. | 5-7 days |
| Embodiment 3 | 18 mM | 250 mM | 4° C. | 19-20 days |
| Embodiment 4 | 18 mM | 25 mM | 37° C. | 8-10 days |
| Embodiment 5 | 1.8 mM | 250 mM | 37° C. | 7-20 days |
| Embodiment 6 | 18 mM | 2.5 mM | 37° C. | 20 days or more |
| Embodiment 7 | 0.18 mM | 250 mM | 37° C. | 20 days or more |
| Embodiment 8 | 0.018 mM | 250 mM | 37° C. | 20 days or more |
| Embodiment 9 | 18 mM | 250 mM | 70° C. | 3 hours |

From the results of Embodiments 1~3, the reaction temperature greatly influences the polymerization rate of melamine. As the reaction temperature increases, the time that the precipitate is observable becomes shorter. FIG. 2 shows the changes of absorbance at 600 nm for the reaction samples in Embodiments 1~3. The higher polymerization degree of melamine leads to the muddier reaction solution, and the absorbance value thereof at 600 nm is also increased. Hence, the absorbance value of the reaction solution can represent the polymerization degree of melamine. From the results shown in FIG. 2, the reaction solution containing 18 mM of melamine and 250 mM of glutaraldehyde at 37° C. (Embodiment 1) reached the maximum polymerization degree at the seventh day. If the polymerization reaction was performed at 24° C. (Embodiment 2), the maximum polymerization degree was at about the tenth day. If the polymerization reaction was performed at 4° C. (Embodiment 3), the precipitate was not observable until ca, the twentieth day. While the absorbance changes of the samples of Embodiments 4~9 were not monitored during the course of polymerization, the appearance of white precipitates in these samples can be used as an indicator of the reaction rates. The results above reveal that temperature is a critical factor influencing the reaction rate of melamine polymerization. More specifically, the reaction rate of melamine polymerization, when using glutaraldehyde as the crosslinker, can be accelerated at a higher reaction temperature within the temperature range of the present invention.

Embodiment 10

Animal Immunization

To immunize animals (New Zealand White rabbits and Balb/c mice) with polymerized melamines, the reaction sample prepared from Embodiment 1 was used. Depending on the species of animal to be inoculated, various amounts (mouse: 0.143 mL/each inoculation; rabbit: 0.43 mL/each inoculation) of the reaction sample were added to microfuge vials respectively, washed with $ddH_2O$ for three times, and each of the final precipitates was re-suspended with $ddH_2O$ to a final volume of 0.5 mL and used as the immunogen. For the first immunization, the 0.5-mL immunogen was emulsified with 0.5 mL of complete Freund's Adjuvant and then administered intraperitoneally and subcutaneously to each mouse or intramuscularly and subcutaneously to each rabbit. Four weeks later, a second immunization was performed as the first immunization, except the incomplete Freund's Adjuvant, instead of the complete Freund's Adjuvant, was used. The final booster was given two weeks after the second immunization, using the previous conditions, but this time no adjuvant was included. Three days after the final booster, animals were bled and sera were prepared and stored at 4° C. for further analyses.

<Immunoassay of Melamine>

After series dilutions of the melamine solution, glutaraldehyde was respectively added into the melamine solutions. The final melamine concentrations in the melamine solutions were 1800 ppm, 180 ppm, 18 ppm, 1.8 ppm, 180 ppb, 18 ppb, 1.8 ppb, 0.18 ppb, and 0.018 ppb, as well as the concentration of glutaraldehyde therein was 250 mM. In addition, 250 mM of glutaraldehyde solution was prepared as a control group. After the above solutions was reacted at 70° C. for 4 hours, 10 µL of each the above solution was respectively mixed with 990 µL of double distilled water to become the melamine samples to be measured.

Figure 3:
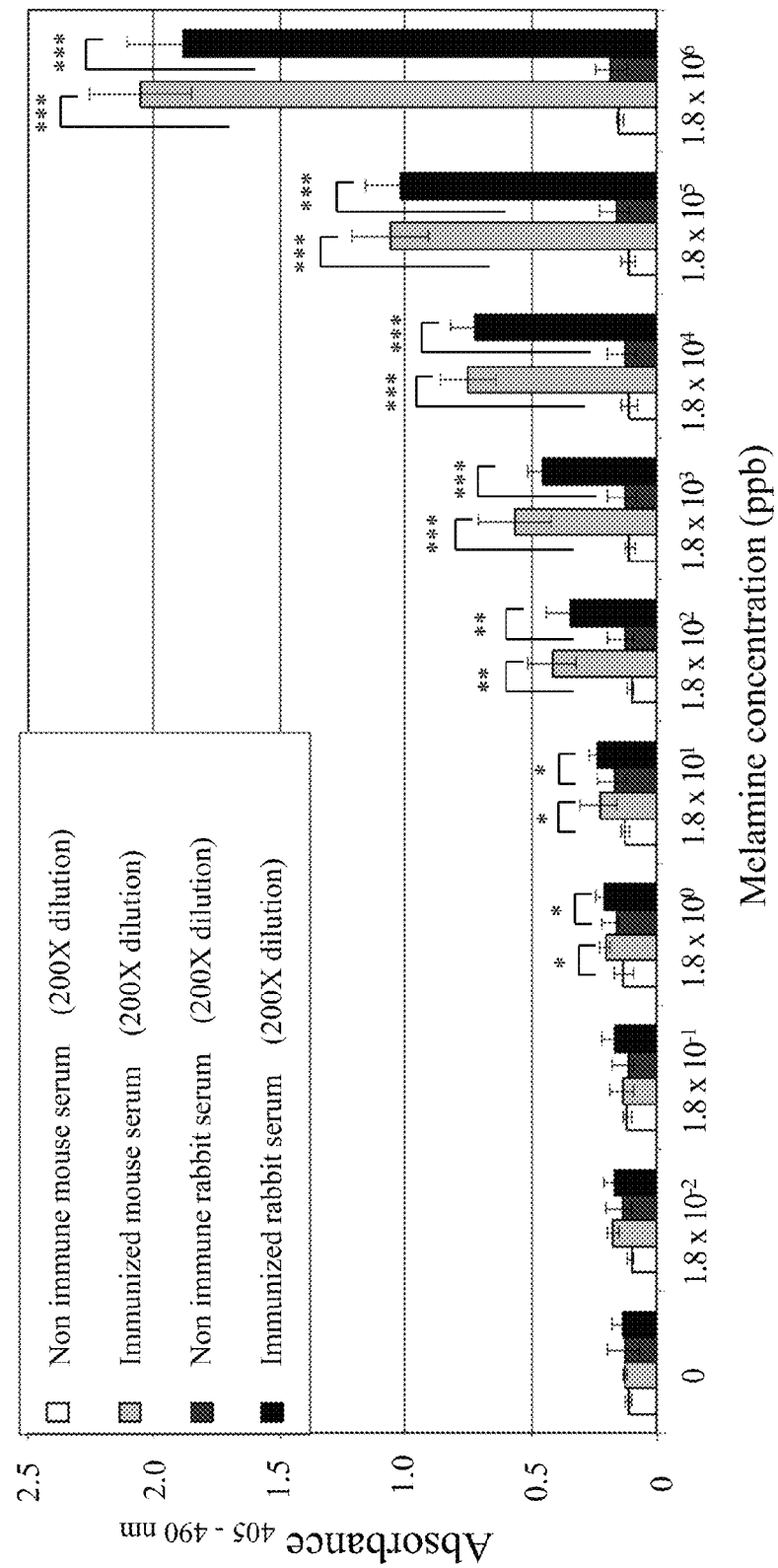
FIG. 3 is a diagram showing the results of immunoassay in Embodiment 10.

50 µL of the primary antibody solution was added into the micro-centrifuge tube containing 200 µL of the melamine samples. After the mixtures were placed at room temperature for 1 hour, the precipitants contained therein were separated with a centrifuge (12000 g, 20 min), the supernatants were discarded, the precipitates were washed with water, and the above procedure was repeated twice. Subsequently, according to the different types of the primary antibodies, 50 µL of different secondary antibodies corresponding to the primary antibodies were added into each tube. For example, when the primary antibody was obtained from the mouse serum, the secondary antibody to be used was rabbit anti-mouse IgG-alkaline phosphatase (Sigma A4312). On the other hand, when the primary antibody was obtained from the rabbit serum, the secondary antibody to be used was goat anti-rabbit IgG-alkaline phosphatase (Sigma A3687). After the samples were placed at room temperature for 1 hour, the precipitants contained therein were separated with a centrifuge (12000 g 20 min), the supernatants were removed, the precipitates were washed with water, and the above procedure was repeated twice. Then, 50 µL of water was used to re-dissolve the precipitate and the samples were added into the wells of ELISA plate. 50 µL of p-Nitrophenyl phosphate (Sigma 50942) solution (0.6 mg/mL) was added into each well and reacted at room temperature for 3 hours. Finally, the absorbance value (405-490 nm) of each samples were measured by an ELISA reader, and the statistical analysis was done by student's t test (n=4, *p<0.05, p<0.01, *p<0.001). As shown in FIG. 3, the results indicate that the serum from the mouse or rabbit that was injected with the polymerized melamine of the present invention can identify melamine effectively, and the minimum detection concentration was 1.8 ppb. For the mouse or rabbit without injection of immunogen, the serum produced therefrom does not react with melamine. The aforementioned result shows that the polymerization method of the present invention can effectively polymerize haptens into an immunogen, which can effectively stimulate the immune systems of animals to produce the corresponding antibodies.

Although the present invention has been explained in relation to its preferred embodiment, it is to be understood that many other possible modifications and variations can be made without departing from the spirit and scope of the invention as hereinafter claimed.

What is claimed is:

1. A method of polymerization of haptens into immunogen, including the steps of: (A) providing a hapten-containing solution, wherein haptens in the hapten-containing solution are chemical compounds with two or more amine groups, chemical compounds with two or more carboxylic groups, or chemical compounds with one or more amine group and one or more carboxylic group; (B) adding a cross-linking reagent into the hapten-containing solution to polymerize the haptens to obtain an immunogen with molecular weight greater than 4000 Da.

2. The method as claimed in claim 1, wherein when the haptens are the chemical compounds having two or more amine groups, the cross-linking reagent is at least one selected from the group consisting of dialdehyde, polyaldehyde, bis-carboxylic acid, and poly-carboxylic acid.

3. The method as claimed in claim 1, wherein when the haptens are the chemical compounds having two or more carboxylic groups, the cross-linking reagent is at least one selected from the group comprising glycol, polyol, bis-amine, and polyamine.

4. The method as claimed in claim 1, wherein when the haptens are the chemical compounds having one or more amine group and one or more carboxylic group, the cross-linking reagent is EDC.

5. The method as claimed in claim 1, wherein when the haptens are the chemical compounds having one or more amine group and one or more carboxylic group, the amine group and the carboxylic group are cross-linked to each other through a dehydration reaction.

6. The method as claimed in claim 1, wherein in the step (A), a hapten concentration in the hapten-containing solution is $1\times10^{-10}$ mM or more.

7. The method as claimed in claim 1, wherein in the step (B), a cross-linking reagent concentration in the hapten-containing solution is $1\times10^{-10}$ mM or more.

8. The method as claimed in claim 1, wherein in the step (A), the haptens are melamine.

9. The method as claimed in claim 8, wherein in the step (B), the cross-linking reagent is glutaraldehyde.

10. The method as claimed in claim 8, wherein in the step (B), the melamine are polymerized at a temperature ranging from 4° C. to 80° C.

11. The method as claimed in claim 8, wherein a melamine concentration in the hapten-containing solution is $1\times10^{-10}$ mM to 24 mM.

12. The method as claimed in claim 9, wherein a glutaraldehyd concentration in the hapten-containing solution is $1\times10^{-10}$ mM to 300 mM.

* * * * *